United States Patent [19]

Ikariya et al.

[11] Patent Number: 5,306,842
[45] Date of Patent: Apr. 26, 1994

[54] METHOD OF MANUFACTURING AROMATIC URETHANES

[75] Inventors: Takao Ikariya; Masanori Itagaki; Masatsugu Mizuguchi; Makoto Miyazawa; Sachiko Yamamoto, all of Tokyo, Japan

[73] Assignee: NKK Corporation, Tokyo, Japan

[21] Appl. No.: 875,459

[22] Filed: Apr. 29, 1992

Related U.S. Application Data

[62] Division of Ser. No. 495,353, Mar. 16, 1990, Pat. No. 5,130,464.

[51] Int. Cl.$^5$ .................. C07C 269/00; C07C 271/00
[52] U.S. Cl. ........................................ 560/24; 560/25; 560/27; 560/28; 560/30; 560/31; 560/32
[58] Field of Search .................. 560/24, 25, 27, 28, 560/30, 31, 32

[56] References Cited

U.S. PATENT DOCUMENTS

| | | | |
|---|---|---|---|
| Re. 34,137 | 12/1992 | Ikariya et al. | 560/24 |
| 2,409,712 | 10/1946 | Schweitzer | 260/453 |
| 2,677,698 | 5/1954 | Deutschman et al. | 260/482 |
| 2,871,259 | 1/1959 | Levy | 260/482 |
| 3,993,685 | 11/1976 | Zajacek et al. | 260/471 C |
| 4,178,455 | 12/1979 | Hirai et al. | 560/24 |
| 4,411,820 | 10/1983 | Pretzer et al. | 502/167 |
| 4,474,978 | 10/1984 | Drent et al. | 560/24 |
| 4,491,670 | 1/1985 | Bhaduri et al. | 560/24 |
| 4,600,793 | 7/1986 | Grate et al. | 560/25 |
| 4,603,216 | 7/1986 | Grate et al. | 560/24 |
| 4,629,804 | 12/1986 | Grate et al. | 560/24 |
| 4,678,856 | 7/1987 | Ikariya et al. | 560/24 |
| 4,687,872 | 8/1987 | Grate et al. | 560/25 |
| 4,705,883 | 11/1987 | Grate et al. | 560/25 |
| 4,709,073 | 11/1987 | Grate et al. | 560/24 |

FOREIGN PATENT DOCUMENTS

| | | |
|---|---|---|
| 0071835 | 2/1983 | European Pat. Off. . |
| 195515 | 9/1986 | European Pat. Off. . |
| 250037 | 12/1987 | European Pat. Off. . |
| 0310907 | 4/1989 | European Pat. Off. . |
| 3405582 | 10/1984 | Fed. Rep. of Germany . |
| 47-34341 | 11/1972 | Japan . |

OTHER PUBLICATIONS

C. A. Buchler and D. E. Pearson, *Survey of Organic Chemistry*, p. 927, (1970), John Wiley & Sons, Inc.

*Primary Examiner*—José G. Dees
*Assistant Examiner*—Porfirio Nazario
*Attorney, Agent, or Firm*—Frishauf, Holtz, Goodman & Woodward

[57] ABSTRACT

A method for manufacturing a purified aromatic urethane. Aromatic urethanes are synthesized from a N,N'-disubstituted urea and an organic hydroxyl compound in a reaction medium. The organic hydroxyl compound and the primary aromatic amine side product which are present in the reaction mixture is distilled off and removed from the reaction mixture leaving a distillation bottom. The N,N'-disubstituted urea is separated and removed from the distillation bottom by solvent extraction of the aromatic urethane, and the aromatic urethane in the extract phase obtained in said solvent extraction is separated and purified.

16 Claims, No Drawings

METHOD OF MANUFACTURING AROMATIC URETHANES

This is a division of application Ser. No. 07/495,353, filed Mar. 16, 1990, now U.S. Pat. No. 5,130,464, issued Jul. 14, 1992.

BACKGROUND OF THE INVENTION

1. Field of the Invention

The present invention relates to a method of manufacturing aromatic urethanes.

2. Description of the Related Art

U.S. Pat. No. 4,678,856 discloses a method wherein a primary aromatic amine, an aromatic nitro compound, and carbon monoxide are caused to react together in the presence of a specified catalyst and solvent to produce a N,N'-disubstituted urea, the urea obtained by this method in turn being caused to react with an organic compound containing hydroxyl groups to produce a primary aromatic amine and an aromatic urethane, the aromatic urethane then being separated and recovered from the reaction product. The above U.S. patent also discloses that aromatic amine is used as a solvent, the amount of which is over the quantity specified as being required for the reaction.

In U.S. patent application Ser. No. 07/825,822, an improvement of U.S. Pat. No. 4,678,856 is disclosed wherein nitriles, pyridines, quinolines and cyclic ethers are used as solvents to stabilize the catalyst and prevent it from separating out. Use of such solvents prevent the catalyst from separating out of the system together with crystals of the urea compound product, and permits the catalyst to be re-used.

SUMMARY OF THE INVENTION

The present invention specifically relates to an improvement of the invention described in U.S. patent application Ser. No. 07/825,822, and proposes a different solvent to that disclosed therein.

The first objective of this invention is to provide a method of manufacturing aromatic urethanes in a two-step reaction, which comprises manufacture of ureas by carbonylation and the reaction of the ureas produced using compounds containing hydroxyl groups, thereby improving the overall yield and selectivity, but which also permits ease of recovery of the catalyst and urethanes.

A second objective of this invention is to provide a method of manufacturing aromatic urethanes wherein at least a part of the solvent used in the urea production reaction of the first step consists of a solvent which acts to stabilize the catalyst in solution to prevent it from separating out and also to improve the activity of the catalyst thereof, thereby permitting efficient recycling of catalyst, increasing the rate of the reaction of the first step, and increasing the efficiency of the method.

A third objective of this invention is to provide a method of manufacturing aromatic urethanes which does not involve the use of halogen compounds, whereby the problems inherent in their use are thus avoided.

In order to achieve the above objectives, this invention consists of a method of manufacturing aromatic urethanes which comprises three processes.

In the first process, an aromatic nitro compound, an aromatic primary amine and carbon monoxide are caused to react together by use of a catalyst comprising a compound containing a platinum group metal, thereby producing N,N'-disubstituted urea. The solvent used here consists at least partly of a solvent (referred to hereafter as a first solvent) which stabilizes the catalyst to prevent it from separating out, and increases its activity so as to maintain the catalyst stable in solution and increase the rate of the reaction. The N,N'-disubstituted urea produced is then separated and isolated.

In the second process, the N,N'-disubstituted urea obtained in the first step is caused to react with a compound containing hydroxyl groups to produce a primary aromatic amine and an aromatic urethane, the latter being obtained by separation of the primary aromatic amine.

In the third process, the primary amine separated is recycled to the first process.

Additional objects and advantages of the invention will be set forth in the description which follows, and will in part be obvious from the description, or may be learned through practice of the invention, while the objects and advantages of the invention may be realized and obtained by means of the instrumentalities and combinations specifically pointed out in the appended claims.

DETAILED DESCRIPTION OF THE PREFERRED EMBODIMENTS

We shall now describe this invention in more detail.

In the first process, an aromatic primary amine, an aromatic nitro compound and carbon monoxide are caused to react together by use of a catalyst consisting essentially of a platinum group metal, and by use of the first solvent having a coordination ability to catalyst metal as at least part of the solvent. This reaction is considered to proceed according to the following equation:

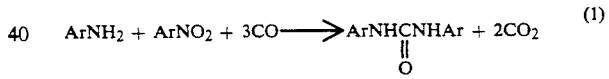

$$\text{ArNH}_2 + \text{ArNO}_2 + 3\text{CO} \longrightarrow \text{ArNHCNHAr} + 2\text{CO}_2 \quad (1)$$
$$\overset{\|}{\underset{\text{O}}{}}$$

The aromatic primary amine can be any one of anilines, aminonaphthalenes, aminoanthracenes and aminobiphenyls, specific examples of such compounds being aniline, o-, m-and p-toluidine, o-, m- and p-chloroaniline, α and β naphthylamine, 2-methyl-1-aminonaphthalene, isomers of diaminobenzene, isomers of triaminobenzene, isomers of aminotoluene, isomers of diaminotoluene, isomers of aminonaphthalene, or mixtures of these compounds.

The aromatic nitro compound can be any one of nitrobenzenes, nitronaphthalenes, nitroanthracenes, nitrobiphenyls, and a nitro-compound wherein at least one of the hydrogen atoms is substituted by for example a halogen atom, cyano group, alicyclic group, aromatic group, alkyl group, alkoxy group, sulfone group, sulfoxide group, carbonyl group, ester group, amide group, or the like, specific examples of such compounds being nitrobenzene, o-, m-, and p-nitrotoluene, o-nitro-p-xylene, 2-methyl-1-nitronaphthalene, isomers of dinitrobenzene, isomers of trinitrobenzene, isomers of dinitrotoluene, isomers of nitronaphthalene, o-, m-, and p-chloronitrobenzene, 1-bromo-4-nitrobenzene, or mixtures of these compounds. The nitro compound use should preferably correspond with the primary aromatic amine.

An amide compound added as first solvent can be any amide, specific examples being N,N-dimethylacetamide, N,N-dimethylformamide, and N-methyl-2-pyrolidinone; a substituted urea represented by the general formula:

where $R^1$, $R^2$, $R^3$, and $R^4$ are alkyl groups and alkylene groups with a carbon chain of 3-5 carbon atoms, specific examples of such compounds being N,N,N',N'-tetramethylurea, 1,3-dimethyl-2-imidazolidinone, 1,3-dimethyl-tetrahydro-2(1H)-pyrimidinone; a phosphineamide compound represented by the general formula:

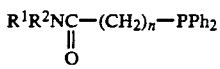

where $R^1$ and $R^2$ are alkyl groups with 1-5 carbon atoms, and $n=1-5$; a phosphine-amide compound represented by the general formula:

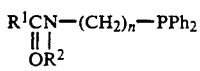

where $R^1$ and $R^2$ are alkyl groups with 1-6 carbon atoms, and alkylene groups with a chain of 3-5 carbon atoms; or isomers or mixtures of these compounds.

An oxygen-containing organic sulfur compound used as first solvent comprises a sulfoxide represented by the general formula $R^1\text{-SO-}R^2$ or $R^1\text{-SO}_2\text{-}R^2$, wherein $R^1$ and $R^2$ are alkyl, alkoxy substituted, phenyl substituted groups with 1-8 carbon atoms, and alkylene groups with a chain of 4-7 carbon atoms, specific examples being dimethylsulfoxide, diphenylsulfoxide and sulfolane.

In this invention, the reaction of the first step may be carried out using a solvent consisting substantially of the first solvent, or may be carried out in a mixture of the first solvent with other suitable solvents. These other suitable solvents comprises an excess of aniline (referred to hereafter as a secondary solvent) compared to the theoretical quantity required for the reaction; compounds which do not contribute to the reaction, examples of which are aromatic hydrocarbons such as benzene, toluene, and xylene; halogenated aliphatic hydrocarbons such as mesitylene chlorohexane and chlorocyclohexane; and halogenated aromatic hydrocarbons such as chlorobenzene, bromobenzene, dichlorobenzene and trichlorobenzene (referred to hereafter as a tertiary solvent).

The carbon monoxide used may be pure, or it may contain nitrogen, argon, helium, carbon dioxide, or halogenated hydrocarbons.

The catalyst containing ruthenium or rhodium is a compound of ruthenium or rhodium with a ligand such as carbon monoxide or a phosphine, or with an organometallic compound containing organic groups, but it is preferable that this compound does not contain halogen atoms. Specific examples of such compounds are ruthenium complexes such as $Ru_3(CO)_{12}$, $H_4Ru_4(CO)_{12}$, $[Ru_2(CO)_4(HCOO)_2]_n$, $Ru(CO)_3(dppe)$, $Ru(CO)_3(PPh_3)_2$ and $Ru(acac)_3$; and rhodium complexes such as $Rh_6(CO)_{16}$, $RhH(CO)(PPh_3)_3$, $Rh(acac)(CO)(PPh_3)$, $Rh(acac)(CO)_2$ and $Rh(acac)_3$. $PPh_3$ indicates triphenylphosphine, dppe indicates diphenylphosphinoethane, and acac indicates acetylacetonate.

In place of these complexes, inorganic platinum group metal compounds may be used which change into reactive species in the reaction system. Specific examples of such compounds are $RuO_2.nH_2O$, Ru-black, and Ru carbon. These compounds change into carbonyl complexes to produce active species in the reaction system.

These platinum group metal compounds may also be used in combination with cobalt, iron, rhodium and palladium compounds or the like.

The reaction temperature is normally in the range 30°-300° C., and preferably 120°-200° C. The reaction pressure is in the range 1-500 kg/cm², and preferably 10-150 kg/cm². The reaction time varies according to reaction temperature, pressure, and other conditions, but normally takes from several minutes to several hours.

The N,N'-substituted urea obtained by the method of this invention has low solubility in solvents and in the aromatic amines and aromatic nitro-compounds which are used as starting materials. Therefore after the reaction is complete and the solution cooled to room temperature, the N,N'-substituted urea crystallizes and separates out, and may thus be obtained in solid form in good yield by filtering the solution. Since the catalyst has been stabilized by the addition of the first solvent, and remains in the filtrate without separating out, it can thus be re-used as it is. Further, as the first solvent increases the activity of the catalyst, the reaction rate at which the reaction of the first step takes palace is high. Since the first solvent has high solubility in the N,N'-substituted urea produced by the reaction, a volume of crystallized N,N'-substituited urea may be controlled by adjusting an amount of the secondary and/or tertiary solvent.

After the reaction, when the solution is cooled to room temperature and the product is crystallized out, constituents of the reaction mixture apart from the di-substituted urea may easily be separated by rinsing with solvents such as toluene and benzene, and the disubstituted urea may therefore be obtained on its own.

Next, in the second process, the N,N'-disubstituted urea obtained is made to react with an organic compound containing hydroxyl groups according to the following equation, to produce a primary aromatic amine and an aromatic urethane:

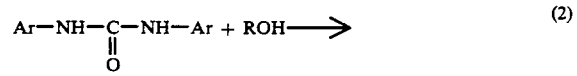

(2)

Ar—NHCOOR + Ar—NH₂

In this reaction, the N,N'-disubstituted urea used as starting material is one substituted on nitrogen atom by organic groups chosen from among aliphatic groups, alicyclic groups, or aromatic groups. The substituting groups may be either identical or different, but at least one of them should be aromatic. The N,N'-disubstituted ureas may be N,N'-diaryl ureas, with ureas having amino substituents on the aromatic ring—such as, for example N,N'-diphenylurea—being particularly suitable.

The organic compound containing hydroxyl groups of this invention may, for example, be a monohydric alcohol, a polyhydric alcohol, or a monohydric or polyhydric phenol, and of these, a monohydric alcohol, a phenol, or a mixture of the two is to be preferred. Specific examples of monohydric alcohols are methyl alcohol, ethyl alcohol, n-propyl alcohol, isopropyl alcohol, n-butyl alcohol, isobutyl alcohol, and t-butyl alcohol. Specific examples of monohydric phenols, apart from phenol itself, are chlorophenol, phenols with alkyl groups such as methyl, ethyl, n-propyl, and isopropyl, and their isomers. Alcohols are to be preferred to phenols, and methanol and ethanol are to be particularly preferred.

The reaction which produces an aromatic urethane from a N,N'-disubstituted urea and an organic compound containing hydroxyl groups is reversible, and in this invention, the equilibrium between the forward and back reactions is controlled by the amount of organic hydroxyl compounds in the reaction system. The reaction equivalents are 1 mole of hydroxyl compound per 1 mole of N,N'-disubstituted urea, but to promote the forward reaction, a large excess of hydroxyl compound must be used. Thus, in this invention, 1-100 moles of hydroxyl compound is used per 1 mole of N,N'-disubstituted urea. As an indication, the amount of hydroxyl compound used must be such that the molar ratio of aromatic urethane (X) to N,N'-disubstitued urea (Y) in the production system, (X/Y), is no less than 20 and preferably in the range of 20-50.

The above urethane synthesis reaction proceeds under the following conditions. The reaction temperature is in the range 80°-300° C., and preferably 120°-200° C. The reaction pressure is the autogenous pressure at the reaction temperature employed—for example, in the range 1-200 atm, and preferably 1-50 atm. The reaction time varies according to reaction temperature, pressure and other conditions, and also according to the type of N,N'-disubstituted urea and organic hydroxyl compound, but normally takes from several minutes to several hours.

In this invention, the desired aromatic urethane is separated from unreacted N,N'-disubstituted urea, concurrently formed primary amine, and organic hydroxy compound as follows. Of the above three compounds, the organic hydroxyl compound and the aromatic primary amine are removed by continuous or batch distillation. Whichever of these distillation methods is used, the number of theoretical plates, the reflux ratio, and the level of internal column pressure may be chosen arbitrarily, provided that the aromatic urethane—remaining at the bottom during continuous distillation or as a still residue in the case of batch distillation—does not decompose and the N,N'-disubstituted urea does not separate out. However, as aromatic urethanes decompose rather easily, it is therefore preferable that the internal column pressure be no greater than 760 mmHg. Further, while the use to which the organic hydroxyl compound and primary aromatic amine ar put after they have been removed by distillation is a matter of choice, it is, however advantageous if they are re-used as reaction starting materials employed in the first step; in particular, it is preferable that the organic hydroxy compound be recycled into the reaction system and reused in this manner.

After the above three compounds have been removed by distillation, the only substantial compound remaining in the reaction system is the N,N'-disubstituted urea, any other compounds present in the reaction system will be only a trace amount of reaction by-products. In the present invention, the desired aromatic urethane is separated from all remaining compounds by solvent extraction, this being accomplished by adding a suitable solvent to the production system, to selectively extract the urethane. The solvent used for this may be chosen from among a number of types, all of which are capable of selectively extracting the urethane; several of these solvents may be mixed together. However, of the various solvents suitable for this purpose, organic solvents such as n-hexane, cylcohexane, benzene toluene, and dichlorobenzene are particularly preferable.

The above solvent extraction process is carried out at a temperature in the range 0°-150° C., and preferably 15°-100° C. The extraction pressure is the autogenous pressure of the system. As before, the extraction time varies according to the reaction temperature and pressure, and also according to the type of the N,N'-disubstituted urea and the aromatic urethane, but normally takes from several minutes to several hours. This extraction process also may be a continuous or a batch operation. The extract phase obtained from the above solvent extraction process is a mixture of the solvent used and the extracted aromatic urethane. The extract residue, on the other hand, is the N,N'-disubstituted urea, or in some cases a mixture of the N,N'-disubstituted urea and minute amounts of side products, and may be either a liquid or solid.

Next, the aromatic urethane is recovered from the extract phase and purified. This may be done by means of distillation, recrystallization and/or crystallization. The choice of method used and the operating conditions are based on the physical properties of the solvent and of the aromatic urethane (vapor-liquid equilibrium, solid-liquid equilibrium and thermal stability, etc). If, for example, the thermal stability of the aromatic urethane is low, cooling crystallization is used. Further, this process is used for solvent-aromatic urethane systems even in which the solubility of the aromatic urethane varies markedly. Distillation, recrystallization, or crystallization may be either continuous or batch operations.

In this invention, as stated earlier, the method of using the extract residue is a matter of choice. However, since the residue consists of N,N'-disubstituted urea, which is a starting material of the second reaction step, and since any other substances present therein, will be only a trace amount of reaction byproducts, it is therefore preferable that this residue be recycled back into the reaction system of the second reaction step, and re-used in this manner.

Similarly, the use made of the liquid remaining after the aromatic urethane has been recovered and purified from the extract phase is a matter of choice; however, it is preferable that it too be recycled, and re-used as extraction solvent.

When the first process (reaction equation (1)) and the second process (reaction equation (2)) are carried out in sequence, the primary aromatic amine does not undergo any actual change, and only the aromatic nitro-compound enters into the reaction. Overall, the aromatic nitro-compound is reductively transformed into the aromatic urethane, and this is more economical than using the primary aromatic amine as a starting material.

To summarize the advantages of this invention, therefore, since the N,N'-disubstituted urea produced in the first reaction step has low solubility in the solvent and the primary aromatic amine or aromatic nitro-compound, it can be easily crystallized by cooling to room temperature, and recovered in good yield by filtering. Further, since the activity of the catalyst is also improved by the first solvent, the reaction efficiency of the first step is increased. Moreover, since the catalyst stabilized by the first solvent is in the form of a solution, it can be re-used in the first reaction step economically.

In addition, as there is no need to use halogen compounds in this invention, little corrosion of the equipment material occurs, and thus there is no need for the reaction vessel be made from high-cost material.

Also, as few side reactions occur in the first reaction step, the N,N'-disubstituted urea may be obtained in high yield.

Further, as there is no need to use a catalyst in the second reaction step, the aromatic urethane may be recovered as a distillation residue instead of it having to be distilled off. Moreover, as the primary aromatic amine which is distilled and the organic compound with hydroxyl groups have relatively low boiling points, the distillation may be conducted under mild conditions, thus making the operation easy to perform. Additionally, the primary aromatic amine which is recovered may be re-used for the production of the N,N'-disubstituted urea of the first reaction step. Finally, the second reaction step takes place without a catalyst, proceeds almost constantly and produces few side products. Consequently although the reaction is two-step, the aromatic urethane may be manufactured in high yield.

EXAMPLES

We shall now describe specific examples of this invention. Instead of using the common generic name "urethane" in these examples, we shall use the term "N-alkyl carbamate" and clearly define the names of each substance.

EXAMPLE 1

Into a 200 ml autoclave equipped with a magnetic stirrer were introduced 5.6 g of nitrobenzene, 7.8 g of aniline, 27 ml of toluene, 6.3 g of N,N,N',N'-tetramethylurea (referred to hereafter as TMU), and 20 mg of $Ru_3(CO)_{12}$. Thereafter the atmosphere within the system was changed to one of carbon monoxide, within was set at a pressure of 50 kg/cm$^2$. Subsequently the reaction was carried out at 160° C. for 2 hours, with continuous stirring. After completion of the reaction, the system was cooled to room temperature, and following gas evacuation, the reaction liquor was filtered and 3.5 g of N,N'-diphenyl urea crystals obtained. The filtrate was analyzed by gas chromatography and high speed liquid chromatography, and found to contain 0.1 g of N,N'-diphenyl urea and 2.9 g of nitrobenzene. This indicated that the TOF (Turn Over Frequency) of N,N'-diphenyl urea production was 100 h$^{-1}$ based on catalyst metal atoms, and the selectivity based on nitrobenzene was 94%.

Next, 3.0 g of the isolated N,N'-diphenyl urea crystals were placed along with 50 g of methanol in another 200 ml autoclave equipped with a magnetic stirrer, and a reaction was carried out at 160° C. for 3 hours. After this reaction was complete, the reaction liquor was analyzed by gas chromatography, which indicated that the yield of methyl N-phenylcarbamate was 96%, and the yield of aniline was 95%.

EXAMPLE 2

The experimental production of N,N'-diphenyl urea was carried out using the same equipment and method as in Example 1, except that the quantity of TMU was 16.4 g and the quantity of toluene was 15 ml. The results of this experiment are shown in Table 1.

Further, 3.0 g of the isolated diphenyl urea and 50 g of methanol were made to react together, using the same equipment and method as in Example 1. The yields of methyl N-phenyl carbamate and aniline were respectively 95% and 94%.

COMPARATIVE EXAMPLE 1

The experimental production of N,N'-diphenyl urea was carried out using the same equipment and method as in Example 1, except that no TMU was added, and the quantity of toluene was 32 ml. The results of this experiment also are shown in Table 1.

COMPARATIVE EXAMPLE 2

The experimental production of N,N'-diphenyl urea was carried out using the same equipment and method as in Example 1 except that pyridine was added instead of TMU. The results of this experiment also are shown in Table 1.

COMPARATIVE EXAMPLE 3

The experimental production of N,N'-diphenyl urea was carried out using the same equipment and method as in Example 1 except that benzonitrile was added instead of TMU. The results of this experiment also are shown in Table 1.

EXAMPLES 3-8

The experimental production of N,N'-diphenyl urea was carried out using the same equipment and method as in Example 1, except that the first solvent used in the previous examples was changed to DMI or NMP in Example 4-8. The results of this experiment are shown in Table 2.

Further, 3.0 g of the isolated diphenyl urea and 50 g of methanol were made to react together, using the same equipment and method as in Example 1, to experimentally produce methyl N-phenyl carbamate and aniline. The results of this experiment are shown in Table 3.

EXAMPLE 9

The experimental production of N,N'-diphenyl urea was carried out using the same equipment and method as in Example 1 except that the catalyst was changed to $[Ru_2(CO)_4(HCOO)_2]_n$. The results of this experiment are shown in Table 4.

Further, 3.0 g of the isolated diphenyl urea and 50 g of methanol were made to react together, using the same equipment and method as in Example 1. The yields of methyl N-phenyl carbamate and aniline were each 95%.

EXAMPLE 10

Synthesis Reaction for Aromatic Urethanes

The reaction was carried out using the following starting materials and under the following conditions:

Starting Materials

-continued

| | |
|---|---|
| N,N'-diphenyl urea: | 20 g |
| Ethanol: | 50 ml |
| Conditions | |
| Reaction temperature: | 170° C. |
| Reaction time: | 180 min |
| Pressure: | Autogenous |
| Reaction vessel: | 200 ml autoclave with magnetic stirrer |

In this reaction, the conversion of N,N'-diphenyl urea (referred to hereafter as DPU) was 97.5%, and that yield of the ethyl ester of N-phenyl carbamate (referred to hereafter as EPC), which was the desired product, was also 97.5%. The selectivity of EPC in this reaction therefore was 100%.

Removal of Impurities by Distillation, 1

1 l of reaction product obtained as above was distilled under the following conditions:

| Starting material composition (mole %): | |
|---|---|
| Ethanol | 79.1 mole % |
| Aniline | 10.3 mole % |
| EPC | 10.3 mole % |
| DPU | 0.3 mole % |
| Amount introduced: | 1 l |
| Type of distillation: | Batch |
| Number of theoretical plates: | 10 |
| Reflux ratio: | 5 |
| Pressure at top of column: | 50 mmHg |

After distillation of 80 mole %, the compositions of the distillate and of the still residue were examined, and the following results were obtained:

| Constituent | Distillate | Still Residue (mole %) |
|---|---|---|
| Ethanol | 98.9 mole % | 0 mole % |
| Aniline | 1.1 mole % | 47.0 mole % |
| EPC | 0 mole % | 51.5 mole % |
| DPU | 0 mole % | 1.5 mole % |

Removal of Impurities by Distillation, 2

The still residue obtained as above was distilled under the following conditions:

| | |
|---|---|
| Amount introduced: | 200 ml |
| Type of distillation: | Batch |
| Number of theoretical plates: | 10 |
| Reflux ratio: | 5 |
| Pressure at top of column: | 5 mmHg |

After distillation of 48 mole %, the compositions of the distillate and of the still residue were examined, and the following results were obtained:

| Constituent | Distillate | Still Residue |
|---|---|---|
| Aniline | 97.9 mole % | 0 mole % |
| EPC | 2.1 mole % | 97.1 mole % |
| DPU | 0 mole % | 2.9 mole % |

Removal of DPU by Solvent Extraction

To 50 g of the still residue obtained in the "Removal of Impurities by Distillation, 2" above, was added 120 g of n-hexane. After heating to 60° C., a solid-liquid separation was performed in a centrifugal filter, with this temperature being maintained. The amounts of filtrate and solid phase recovered, and the compositions thereof, were as follows:

| | Filtrate | Solid Phase |
|---|---|---|
| Amount recovered (g) | 168.6 g | 1.4 g |
| Composition: | | |
| n-hexane | 71.1 mole % | 5.0 mole % |
| EPC | 28.8 mole % | 2.1 mole % |
| DPU | 0.1 mole % | 92.9 mole % |

Purification of EPC 100 g of the filtrate obtained above were cooled from 60° C. to 25° C., and a solid-liquid separation was performed in a centrifugal filter, with the temperature of 25° C. being maintained. The amounts of filtrate and solid phase recovered, and the compositions thereof, were as follows:

| | Filtrate | Solid Phase |
|---|---|---|
| Amount recovered (g) | 74.3 g | 25.7 g |
| Composition: | | |
| n-hexane | 96.7 mole % | 0 mole % |
| EPC | 3.3 mole % | 99.6 mole % |
| DPU | 0 mole % | 0.4 mole % |

EXAMPLE 11

The filtrate obtained in the "Removal of DPU by Solvent Extraction" of Example 10 was distilled under the following conditions:

| | |
|---|---|
| Amount introduced: | 50 ml |
| Type of distillation: | Batch |
| Number of theoretical plates: | 10 |
| Reflux ratio: | 5 |
| Pressure at top of column: | 5 mmHg |

After distillation of 72 mole %, the compositions of the distillate and of the still residue were examined, and the following results were obtained:

| Constituent | Distillate | Still Residue |
|---|---|---|
| n-hexane | 98.9 mole % | 0 mole % |
| EPC | 1.2 mole % | 99.6 mole % |
| DPU | 0 mole % | 0.4 mole % |

EXAMPLE 12

Synthesis Reaction for Aromatic Urethanes

The reaction was carried out with the following starting materials and under the following conditions:

| | |
|---|---|
| Starting Materials | |
| N,N'-diphenyl urea: | 5 g |
| Methanol: | 50 ml |
| Conditions | |
| Reaction temperature: | 140° C. |
| Reaction time: | 120 min |
| Pressure: | Autogenous |
| Reaction vessel: | 200 ml autoclave with magnetic stirrer |

In this reaction, the conversion of N,N'-diphenyl urea (referred to hereafter as DPU) was 95.3%, and the yield of the methyl ester of N-phenyl carbamate (referred to hereafter as MPC), which was the desired product, was 95.0%. The selectivity of MPC in the reaction was therefore 99.7%

Removal of Impurities by Distillation, 1

1 l of reaction product obtained as above was distilled under the following conditions:

| Starting material composition (mole %): | |
|---|---|
| Methanol | 93.5 mole % |
| Aniline | 3.2 mole % |
| EPC | 3.2 mole % |
| DPU | 0.1 mole % |
| Amount introduced: | 1 l |
| Type of distillation: | Batch |
| Number of theoretical plates: | 10 |
| Reflux ratio: | 5 |
| Pressure at top of column: | 50 mmHg |

After distillation of 94 mole %, the compositions of the distillate and of the still residue were examined, and the following results were obtained:

| Constituent | Distillate | Still Residue (mole %) |
|---|---|---|
| Methanol | 99.5 mole % | 0 mole % |
| Aniline | 0.5 mole % | 45.0 mole % |
| MPC | 0 mole % | 53.3 mole % |
| DPU | 0 mole % | 1.7 mole % |

Removal of Impurities by Distillation, 2

The still residue obtained above was distilled under the following conditions:

| Amount introduced: | 50 ml |
|---|---|
| Type of distillation: | Batch |
| Number of theoretical plates: | 10 |
| Reflux ratio: | 5 |
| Pressure at top of column: | 5 mmHg |

After distillation of 46 mole %, the compositions of the distillate and of the still residue were examined, and the following results were obtained:

| Constituent | Distillate | Still Residue |
|---|---|---|
| Aniline | 97.8 mole % | 0 mole % |
| EPC | 2.2 mole % | 96.9 mole % |
| DPU | 0 mole % | 3.1 mole % |

Removal of DPU by Solvent Extraction

To 25 g of the still residue obtained in the "Removal of Impurities by Distillation, 2" above was added 60 g of n-hexane. After heating to 60° C., a solid-liquid separation was performed in a centrifugal filter, with this temperature being maintained. The amounts of filtrate and solid phase recovered, and the compositions thereof, were as follows:

| | Filtrate | Solid Phase |
|---|---|---|
| Amount recovered (g) | 84.1 g | 0.9 g |
| Composition: | | |
| n-hexane | 71.2 mole % | 0.6 mole % |
| EPC | 28.7 mole % | 0.2 mole % |
| DPU | 0.1 mole % | 99.2 mole % |

Purification of MPC 50 g of the filtrate obtained above were cooled from 60° C. to 15° C., and a solid-liquid separation was performed in a centrifugal filter, with the temperature of 15° C. being maintained. The amounts of filtrate and solid phase recovered, and the compositions thereof were as follows:

| | Filtrate | Solid Phase |
|---|---|---|
| Amount recovered (g) | 37.2 g | 12.8 g |
| Composition: | | |
| n-hexane | 95.7 mole % | 0 mole % |
| MPC | 4.3 mole % | 99.4 mole % |
| DPU | 0 mole % | 0.6 mole % |

As can be seen from Examples 10–12, no catalyst is used in the above two-step process. Consequently, this disperses with the need for complex—and costly—operations for separating and recovering the catalyst from the reaction system, and further, there is no corrosion of metal parts, as would occur were chlorinated catalysts or the like to be used. In addition, the selectivity of the desired aromatic urethanes from N,N'-disubstituted ureas in this invention is high, and there are practically no side products. Therefore aromatic urethanes can be produced in a more cost-efficient manner, since only the organic hydroxyl compounds, aromatic amines, and N,N'-disubstituted ureas have to be removed from the reaction system.

Additional advantages and modifications will readily occur to those skilled in the art. Therefore, the invention in its broader aspects is not limited to the specific details and illustrated examples shown and described herein. Accordingly, various modifications may be made without departing from the spirit or scope of the general inventive concept as defined by the appended claims and their equivalents.

TABLE 1

| | Quantity introduced | | | | | | |
|---|---|---|---|---|---|---|---|
| Example | $Ru_3(CO)_{12}$ (mg) | $PhNO_2$ (g) | $PhNH_2$ (g) | Toluene (ml) | First solvent (g) | TOF ($h^{-1}$) | Selectivity (%) |
| 1 | 20 | 5.6 | 7.8 | 27 | TMU* 6.3 | 100 | 94 |
| 2 | 20 | 5.6 | 7.8 | 15 | TMU 16.4 | 137 | 94 |
| Comparative Example 1 | 20 | 5.6 | 7.8 | 32 | 0 | 56 | 98 |
| 2 | 19 | 5.4 | 9.6 | 21 | Py* 9.2 | 46 | 90 |

TABLE 1-continued

| Example | Ru3(CO)12 (mg) | PhNO2 (g) | PhNH2 (g) | Toluene (ml) | First solvent (g) | TOF ($h^{-1}$) | Selectivity (%) |
|---|---|---|---|---|---|---|---|
| 3 | 20 | 5.5 | 9.5 | 19 | PhCN* 9.6 | 40 | 94 |

TMU: N,N,N',N'-tetramethylurea
Py: Pyridine
PhCN: Benzonitrile

TABLE 2

| Example | Ru3(CO)12 (mg) | PhNO2 (g) | PhNH2 (g) | Toluene (ml) | First solvent (g) | TOF ($h^{-1}$) | Selectivity (%) |
|---|---|---|---|---|---|---|---|
| 3 | 20 | 5.6 | 7.6 | 30 | TMU 2.8 | 76 | 93 |
| 4 | 20 | 5.6 | 7.8 | 23 | TMU 9.0 | 111 | 93 |
| 5 | 20 | 5.6 | 8.2 | 32 | DMI* 3.0 | 90 | 94 |
| 6 | 20 | 5.6 | 8.2 | 23 | DMI 8.9 | 109 | 94 |
| 7 | 20 | 5.6 | 7.9 | 30 | NMP* 3.1 | 92 | 95 |
| 8 | 20 | 5.6 | 9.5 | 23 | NMP 9.3 | 143 | 94 |

DMI: 1,3-dimethyl-2-imidazolidinone
NMP: N-methyl-2-pyrolidinone

TABLE 3

| Example | MPC yield (%) | Aniline yield (%) |
|---|---|---|
| 3 | 95 | 94 |
| 4 | 94 | 94 |
| 5 | 95 | 95 |
| 6 | 93 | 93 |
| 7 | 96 | 94 |
| 8 | 96 | 94 |

MPC: Methyl N-phenyl carbamate

TABLE 4

| Example | Catalyst (mg) | PhNO2 (g) | PhNH2 (g) | Toluene (ml) | First solvent (g) | TOF ($h^{-1}$) | Selectivity (%) |
|---|---|---|---|---|---|---|---|
| 3 | A 20 | 5.6 | 7.6 | 30 | TMU 2.8 | 76 | 93 |
| 9 | B 20 | 5.6 | 7.7 | 27 | TMU 2.6 | 86 | 98 |

A: Ru3(CO)12
B: [$_{Ru2}$(CO)4(HCOO)2]n

What is claimed is:

1. A method for manufacturing an aromatic urethane, wherein said urethane is synthesized without the use of a catalyst, and the urethane produced is purified, said method comprising:
   (a) reacting a N,N'-disubstituted urea and an organic hydroxyl compound to form a reaction mixture containing an aromatic urethane and as a by-product, a primary aromatic amine,
   (b) distilling the reaction mixture from step (a) to distill off and remove said organic hydroxyl compound and the primary aromatic amine, wherein a distillation bottom product is formed, said distilling being performed under a reduced pressure, whereby the boiling point of the aromatic urethane decreases to its decomposing temperature thereof or less, so as to prevent the decomposition of the aromatic urethane in the reaction mixture,
   (c) separating and removing the N,N'-disubstituted urea from the distillation bottom product obtained in step (b), by solvent extraction to form an extract phase, and
   (d) separating and purifying the aromatic urethane in the extract phase.

2. The method according to claim 1, wherein said step (a) is carried out at a temperature of 100°-300° C. and a pressure of 1-200 atm.

3. The method according to claim 1, wherein said step (d) for separating and purifying the aromatic urethane comprises distillation, recrystallization and crystallization processes.

4. The method according to claim 1, wherein in said step (a) the N,N'-disubstituted urea is a N,N'-diaryl urea.

5. The method according to claim 1, wherein in said step (a) said organic hydroxyl compound is selected from the group consisting of monohydric alcohols, polyhydric alcohols, monohydric phenols, polyhydric phenols, and mixtures thereof.

6. The method according to claim 4, wherein the N,N'-diaryl urea is N,N'-diphenylurea.

7. The method according to claim 5, wherein said organic hydroxyl compound is selected from the group consisting of methyl alcohol, ethyl alcohol, n-propyl alcohol, isopropyl alcohol, n-butyl alcohol, isobutyl alcohol, t-butyl alcohol, phenol, chlorophenol and phenol substituted with a alkyl group selected from the group consisting of methyl, ethyl, n-propyl and isopropyl.

8. The method according to claim 7, wherein 1-100 moles of said hydroxyl compound are used per 1 mole of said N,N'-disubstituted urea.

9. The method according to claim 8, wherein step (a) is carried out at a temperature of 120° to 200° C. and at a pressure of 1 to 50 atmospheres.

10. The method according to claim 9, wherein step (c) is carried out at a temperature of 0° to 150° C.

11. The method according to claim 9, wherein step (c) is carried out at a temperature of 15° to 100° C.

12. The method according to claim 11, wherein the N,N'-disubstituted urea is N,N'-diphenylurea and the organic hydroxyl compound is ethanol or methanol.

13. The method according to claim 1, wherein the distilling in step (b) is carried out at a pressure of no greater than 50 mmHg.

14. The method according to claim 13, wherein the pressure is 5 mmHg.

15. The method according to claim 13, wherein the pressure is 5 to 50 mmHg.

16. The method according to claim 1, wherein the N,N'-disubstituted urea is N,N'-diphenyl urea; the organic hydroxyl compound is ethanol; the reaction mixture includes ethanol, aniline, ethyl carbanilate and N,N'-diphenyl urea and the distilling is carried out at a pressure of 50 mmHg or less.

* * * * *